(12) United States Patent
Simmons et al.

(10) Patent No.: US 8,379,208 B1
(45) Date of Patent: Feb. 19, 2013

(54) SYSTEM AND METHOD FOR PASSIVE REMOTE DETECTION OF GAS PLUMES

(75) Inventors: Rulon Eugene Simmons, Rochester, NY (US); Jarett Levi Bartholomew, Victor, NY (US)

(73) Assignee: Exelis, Inc., McLean, VA (US)

( * ) Notice: Subject to any disclaimer, the term of this patent is extended or adjusted under 35 U.S.C. 154(b) by 371 days.

(21) Appl. No.: 12/796,853

(22) Filed: Jun. 9, 2010

(51) Int. Cl.
*G01N 21/35* (2006.01)
(52) U.S. Cl. .................... 356/437; 356/432; 356/434
(58) Field of Classification Search .......... 356/432–437; 250/338.5, 339.13, 330, 334
See application file for complete search history.

(56) References Cited

U.S. PATENT DOCUMENTS

| | | | | |
|---|---|---|---|---|
| 3,735,127 | A * | 5/1973 | Astheimer | 250/346 |
| 3,790,797 | A * | 2/1974 | Sternberg et al. | 250/345 |
| 3,832,548 | A * | 8/1974 | Wallack | 250/343 |
| 3,860,344 | A * | 1/1975 | Garfunkel | 356/51 |
| 4,641,973 | A * | 2/1987 | Nestler et al. | 356/418 |
| 5,036,198 | A * | 7/1991 | Spaeth | 250/343 |
| 5,075,550 | A * | 12/1991 | Miller et al. | 250/338.5 |
| 5,498,872 | A * | 3/1996 | Stedman et al. | 250/338.5 |
| 6,690,472 | B2 * | 2/2004 | Kulp et al. | 356/437 |
| 6,756,592 | B1 * | 6/2004 | Smith et al. | 250/338.5 |
| 6,853,452 | B1 | 2/2005 | Laufer | |
| 7,141,793 | B2 | 11/2006 | Johnson et al. | |
| 7,359,804 | B2 * | 4/2008 | Williams et al. | 702/28 |

* cited by examiner

*Primary Examiner* — Sang Nguyen
(74) *Attorney, Agent, or Firm* — RatnerPrestia (57) ABSTRACT

The present invention includes systems and methods for quantitative and qualitative imaging of gases, vapors, fumes, and the like. In one embodiment, the system uses a moving, or a rotating filter for alternately capturing on-line and off-line images of a scene that potentially includes the target gas of interest. The moving, or rotating filter includes at least two filter segments for transmitting (a) wavelengths corresponding to a spectroscopic absorption feature for on-line elements of the target gas, and (b) nearby wavelengths not corresponding to a spectroscopic absorption feature for off-line elements of the target gas. An image processor executes an algorithm for transforming the collected on-line and off-line data, corresponding to different pixels in the imaging array, into an image map of path-integrated concentration, or concentration path lengths (CPLs). The systems and methods of the invention do not use active light sources to illuminate the target gas. Instead, imaging and processing is done entirely using passive received energy from the target gas.

19 Claims, 7 Drawing Sheets

SYSTEM AND METHOD FOR PASSIVE REMOTE DETECTION OF GAS PLUMES

FIELD OF THE INVENTION

The present invention relates, in general, to passive detection, imaging and measurement of gas plumes. More specifically, the present invention is directed to passive detection and measurement of gas plumes employing two or more filters together with an infrared imaging focal plane array (FPA) and a processing unit. The two filters may be moving or stationary filters, or may be an etalon configured to pass light that is in phase and out of phase having periodic spectral features of a predetermined gas or multiple gases.

BACKGROUND OF THE INVENTION

Gas species typically have unique spectral features in the midwave (3-5 micron) and/or the longwave (8-14 micron) infrared (IR) regions of the electromagnetic spectrum. Whether the spectral features manifest themselves as an emission spectrum or an absorption spectrum depends upon the temperature of the gas relative to its background. If the gas is cooler than the background, the gas exhibits an absorption spectrum. If the gas is warmer than the background, the gas exhibits an emission spectrum with features mirroring the wavelengths of its absorption spectrum. In either case, distinctive features may usually be found that characterize a particular gas. Systems that are tuned to detect the presence or absence of one or more spectral features of the gas so that the particular gas may be identified are known in the art.

A laser system called differential absorption lidar (DIAL) has been effectively used to detect and identify the presence of specific target gas species. The sensitivity of the DIAL system is achieved by performing a comparison between an "on-line" spectral band (that corresponds in wavelength to an absorption feature of the target gas species) and a nearby "off-line" spectral band (that corresponds in wavelength to a non-absorption feature of the target gas species).

DIAL systems, however, tend to be relatively expensive and require active illumination. A less expensive system is, therefore, desirable and would open the door to a variety of new applications. Such a system may include a small portable unit used to detect the presence of harmful gases on a battlefield or at an airport, for example. Another system may be useful in homeland security surveillance, such as at airports, subways, bus stations, naval yard, malls, government buildings, etc.

Furthermore, DIAL systems require active illumination from a laser source. Active illumination is undesirable, since the source of the illumination may potentially be detected by an enemy.

Figure 1:
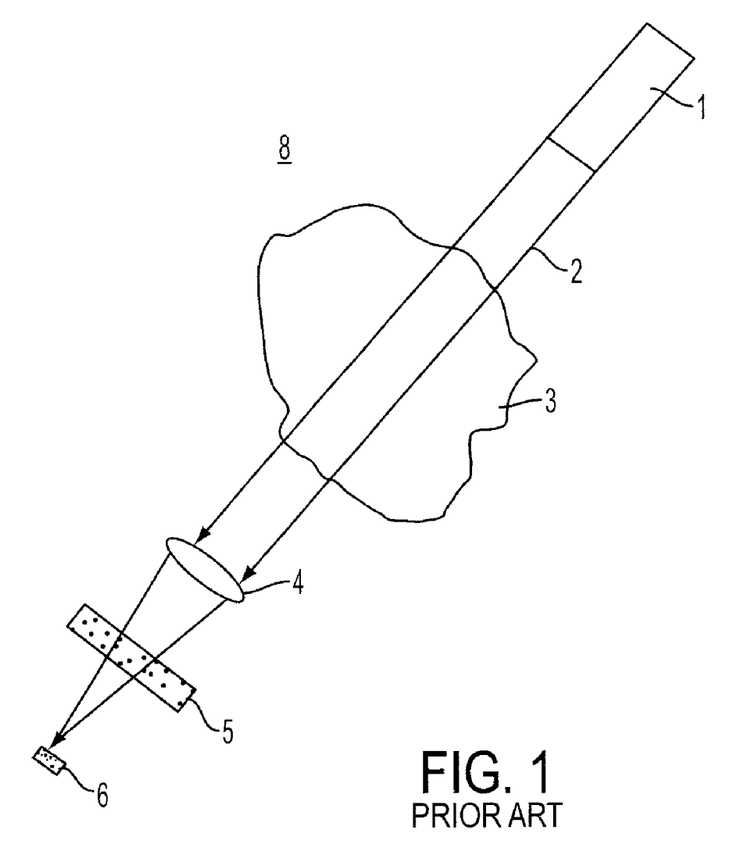
FIG. 1 is a representation of a prior art system in which a beam from an active illumination source is passed through a gas plume and into a detection unit, the latter including a focusing lens, a filter (or filter wheel), and a detector.

Various non-laser IR systems are known for detecting and measuring characteristics of a gas. These systems are also based on an active illumination source that transmits light through a gas. One such system is described in U.S. Pat. No. 7,141,793, which is incorporated herein by reference in its entirety. An example of such a system, designated as 8, is illustrated in FIG. 1 and briefly described below.

The system 8 includes beam 2 from a radiation source 1, which passes through emission plume 3. The beam 2 then passes through a lens 4, a filter wheel 5 and is subsequently detected by a detector 6. The concentrations of various components of the emission plume may be calculated by determining the amount of radiation of certain characteristic wavelengths which have been absorbed from the beam upon its passage through the emission plume.

The system 8 includes a filter wheel 5. As disclosed in the aforementioned patent, the filter wheel may include a set of filters distributed on the filter wheel. The filters on the wheel are rotated so that one filter at a time is aligned with a single detector, such as detector 6. The single detector is assumed to have a sufficiently broad frequency response so that it may cover all of the detection bands of interest. Each of the filters on the wheel allow transmission of only certain wavelengths through the filter wheel. Thus, each of the filters is used to isolate different detection bands of radiation for detection of different components of the emission plume.

In some situations, a sample of the gas plume must be captured in a gas cell. These gas cells typically allow for only a single point measurement. The aforementioned systems, whether they include a gas cell or not, are relatively insensitive. Therefore, these systems require external illumination through the emission plume. Thus, these systems include active sources of illumination, which are undesirable.

The present invention, as will be explained, increases sensitivity of a non-laser gas detector by using a DIAL-like methodology for detecting, measuring and identifying gas plumes. The present invention uses multiple filters, at least one of which is tuned to a spectral characteristic of the target gas (on-line) and at least one of which is tuned to a nearby wavelength in which no absorption occurs in the target gas (off-line).

By using an on-line and off-line filter combination together with subsequent processing, greater sensitivity is achieved by the present invention. As a result, the present invention facilitates detection and measurement of a gas without the requirement of an active illumination source. In fact, the present invention passively samples infrared signatures of the emission plume by using a detector array that produces a spatially-variant result, represented as an image.

SUMMARY OF THE INVENTION

The present invention provides a method and system for detecting and measuring targeted gases, without using active illumination, or using a gas cell to capture the gas.

The embodiments of this invention may vary with different applications, depending upon the width of the spectral features associated with a particular gas. In one embodiment, a calculation of path-integrated concentration of a gas, or the concentration path length (CPL) of the gas is determined using detection results from two separate filters. A gas assessment is accomplished using the two separate filters, including at least two segments on a movable filter, or a rotating wheel. One of the segments includes an on-line filter, which absorbs a feature of the gas of interest; and another of the segments includes an off-line filter which does not absorb features of the gas of interest.

In another embodiment, a multi-segment filter is rotated in front of a detector. The detector records an image through each filter segment. In the case of a spinning filter wheel, a clocking device may be used to sync which filter segment is placed in front of the detector. In this manner, the energy passing through the on-line filter may be integrated during multiple rotations. Similarly, the off-line energy may likewise be integrated during multiple rotations of the wheel.

When sufficient exposure provides an acceptable signal-to-noise ratio, the results of the on-line detection are compared against the off-line detection in order to determine if a gas of interest is present.

Another embodiment of the present invention provides simultaneous detection and measurement of multiple gases by using a filter with multiple sets of on-line and off-line filter segments. As more filter segments are added, the integration time becomes longer in order to compensate for the shorter duration of exposure of each filter segment on the filter wheel.

Yet another embodiment of the present invention uses two side-by-side filters which are alternately moved in front of the FPA sensor, or detector.

In still another embodiment, two separate FPA sensors, one for each filter, is used, thus eliminating moving parts and decreasing the integration time necessary to collect sufficient data. The two resulting images that correspond to the two separate FPA sensors are registered to each other and then further processing may be applied.

Another possible embodiment may use a partially-reflecting mirror to channel a portion of the scene energy through an on-line filter and another portion through an off-line filter.

Each of the foregoing embodiments uses multiple filters which may be formed from dielectric coatings, or other coatings.

Still another embodiment of the present invention, particularly suited to detecting and identifying low molecular weight gases having narrow periodic spectral features, uses an etalon as a Fabry-Perot interferometer to separate on-line and off-line spectra The spectra are then detected and identified by an imaging detector and an image processor, respectively.

BRIEF DESCRIPTION OF THE FIGURES

The present invention may be understood from the following detailed description when read in connection with the following figures.

DETAILED DESCRIPTION OF THE INVENTION

The present invention relates, in general, to passive detection and identification of gas plumes by employing two or more filters in conjunction with an infrared (IR) imaging focal plane array (FPA) and a processing unit. The filters may include two or more segments on a rotating filter wheel. The filters may also include two or more segments on a movable side-by-side filter. Furthermore, the filters may be an etalon configured to pass light that is in phase and out of phase with periodic spectral features of a particular gas of interest. The filters, in general, include at least one set of an on-line filter and an off-line filter, which are used in accordance with various embodiments of the present invention, as described below.

Figure 2:
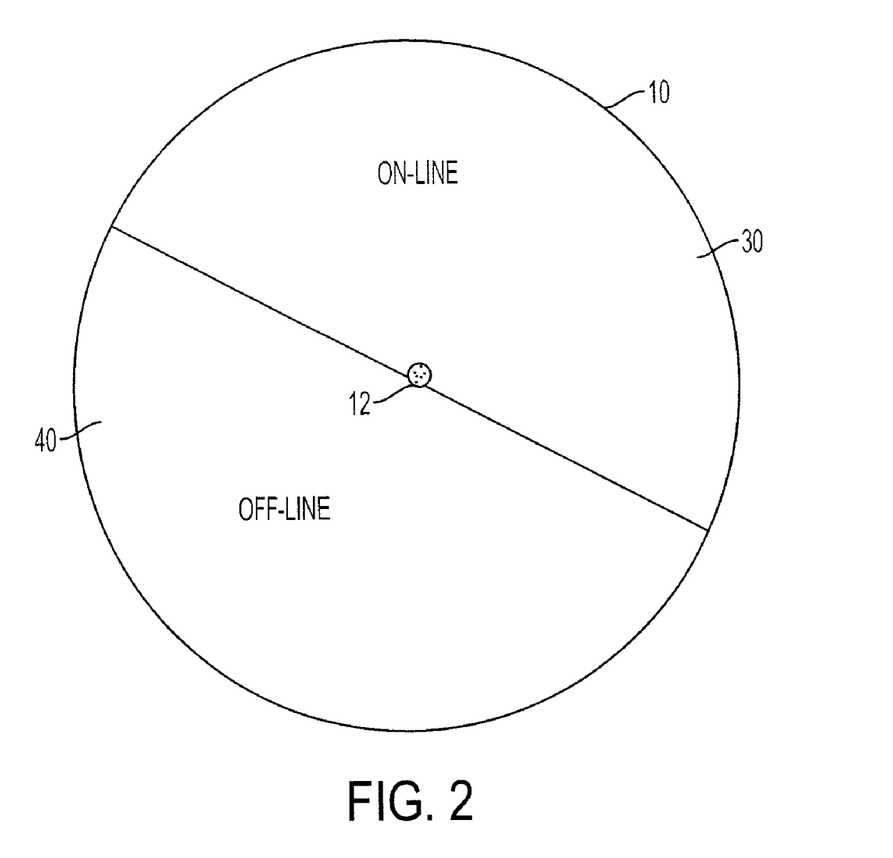
FIG. 2 is a pictorial representation of a rotating filter wheel including two segments, one on-line filter segment and one off-line filter segment, in accordance with an embodiment of the present invention.
Figure 3:
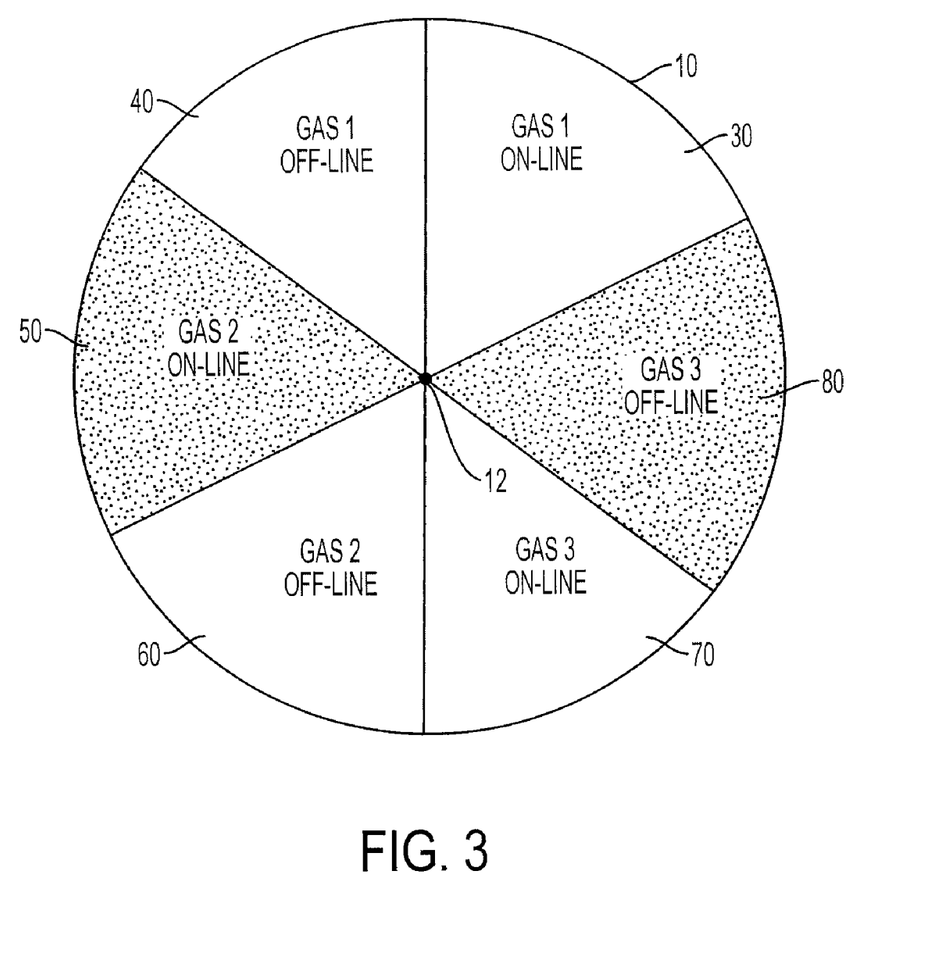
FIG. 3 is a pictorial representation of a rotating filter wheel with more than two segments of one on-line and one off-line filters, for simultaneously detecting multiple gas species, or multiple features of one gas species, in accordance with an embodiment of the present invention.

Referring first to the filters shown in FIGS. 2 and 3, each filter shows at least one on-line filter segment and one off-line filter segment. Two filter segments are shown in FIG. 2. As shown, filter wheel 10 includes an on-line filter segment, designated as 30, and an off-line filter segment, designated as 40. The filter wheel 10 is configured to be rotated on a shaft 12, which may be controlled by a motor (not shown).

FIG. 3 shows a similar filter wheel, also designated as 10, which may be rotated by a shaft 12, the latter controlled by a motor (not shown). Three sets of two filter segments are shown. One set includes an on-line filter 30 and an off-line filter 40 for detecting and identifying the presence or absence of a first gaseous species (shown as gas 1). The next set includes an on-line filter 50 and an off-line filter 60 for detecting and identifying the presence or absence of a second gaseous species (shown as gas 2). Yet another set includes an on-line filter 70 and an off-line filter 80 for detecting and identifying the presence or absence of a third gaseous species (shown as gas 3).

Figure 4:
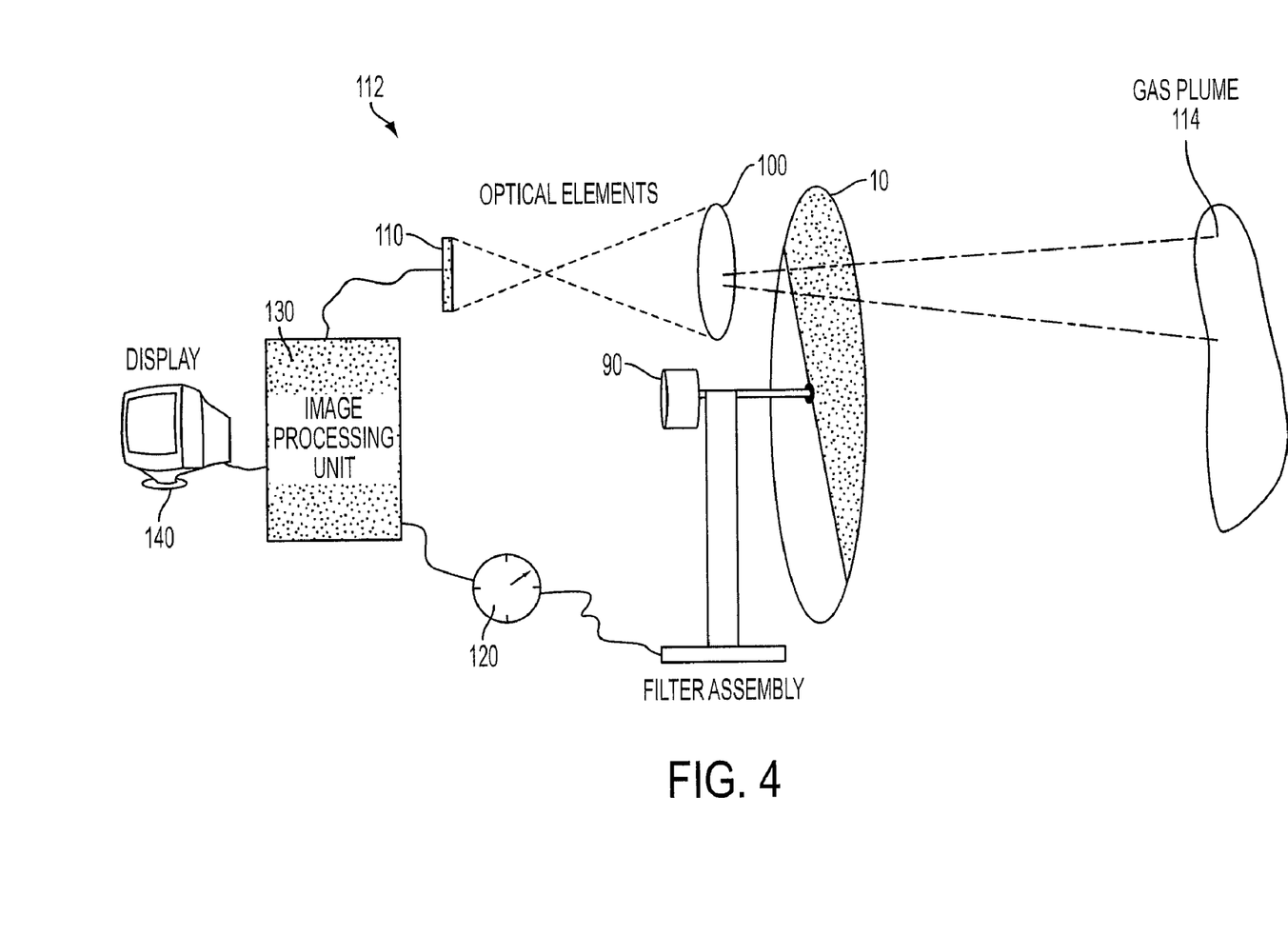
FIG. 4 depicts a system including a rotating filter wheel having multiple segments of one on-line and one off-line filters, providing filtered optical signals to a detector array, an image processing unit and a display, in accordance with an embodiment of the present invention.

Referring now to FIG. 4, there is shown a gas detection and identification system, designated generally as 112. The system includes an imager having optics 100 and a detector array 110, which may be an FPA. The imager is configured to passively detect gas plume 114, after IR energy from the gas plume is filtered by spinning, or rotating filter wheel 10. The filter wheel 10 includes two filter segments, one being an on-line filter 30 and the other being an off-line filter 40 (refer to FIG. 2). The filter wheel 10 may also include more than two filter segments, such as the multiple filter segments depicted in FIG. 3.

The filter wheel 10 is configured to rotate by way of a shaft connected to motor 90. The rotation of filter wheel 10 is synchronized to the received energy detected by detector array 110. The synchronization is controlled by image processing unit 130, which receives intensity data from the various pixels of detector array 110 and controls rotation of filter wheel 10 by way of a synchronization unit 120, which may include a clocking device 120.

The image processing unit 130 processes the intensity data received from detector array 110 and identifies the presence or absence of a particular gas in a manner described later. The image processing unit 110 is also connected to display 140 for interaction with a user.

The image processing unit integrates the received energy filtered by filter wheel 10 relative to the absorption/emission spectrum of the particular gas of interest. The filter wheel 10 is used in conjunction with the imager to detect and record images of a target area formed on detector array 110. Thus, the on-line filter segment of the filter wheel, during a first synchronized interval, is optically aligned with optics 100. During this first interval, detector array 110 is provided with a first level of signal intensities due to an absorption spectrum feature of gas plume 114. The on-line filter passes the first level of signal intensities, if the received energy is, in fact, in the absorption spectrum that characterizes a particular predetermined gas of interest.

Similarly, the off-line filter segment of the filter wheel, during a second synchronized interval, becomes optically aligned with optics 100. During this second interval, detector array 110 is provided with a second level of signal intensities due to a non-absorption spectrum feature of gas plume 114. The off-line filter passes the second level of signal intensities, if the received energy is, in fact, in the non-absorption spectrum of all present gases.

The image processing unit 130 takes the integrated energy from the on-line filter and the off-line filter and processes them to determine the presence or absence of the target gas of interest. An exemplary implementation algorithm executed by the image processing unit may include a DIAL equation which calculates the path-integrated concentration of the gas, also referred to herein as the concentration path length (CPL). The equation is shown below and is calculated for each pixel in detector array 110:

$$CPL_{ij}=1/(2*C\sigma)*ln[(Ef_{ij}/En_{ij})(EIn_{ij}/EIf_{ij})]$$

where:

the subscript $_{ij}$ refers to the coordinates of a particular pixel in the detector array, $CPL_{ij}$ is the path-integrated concentration, or concentration path length, in ppm per meter, along the pixel line of sight from the detector array to the target gas, $C\sigma$ is a calibration constant for the absorption cross section of the particular target species, $Ef_{ij}$ is the image of the target in the off-line wavelength region, $En_{ij}$ is the image of the target in the on-line wavelength region, $EIn_{ij}$ relates to the on-line illumination intensity of the scene, and $EIf_{ij}$ relates to the off-line illumination intensity of the scene.

The ratio $EIn_{ij}/EIf_{ij}$ may often be unity (1), depending on the choice of filter elements.

The data thus acquired by detector array 110 may be divided into two separate data arrays, one on-line data array and another off-line data array. The CPL is then computed by using the data from the two data arrays corresponding to the same pixel coordinates of ij.

The filter wheel 10 may include multiple sets of on-line and off-line filter segments, as shown in FIG. 3. In such a situation, the CPL computations may be based on multiple data arrays captured by detector array 110. Thus, for example, a CPL may be computed for each pixel coordinate in the detector array for the first gas (two data arrays), and another CPL may be computed for each pixel coordinate in the detector array for the second gas (another two data arrays). Furthermore, yet another CPL may be computed for each pixel coordinate in the detector array for the third gas (yet another two data arrays).

Figure 5:
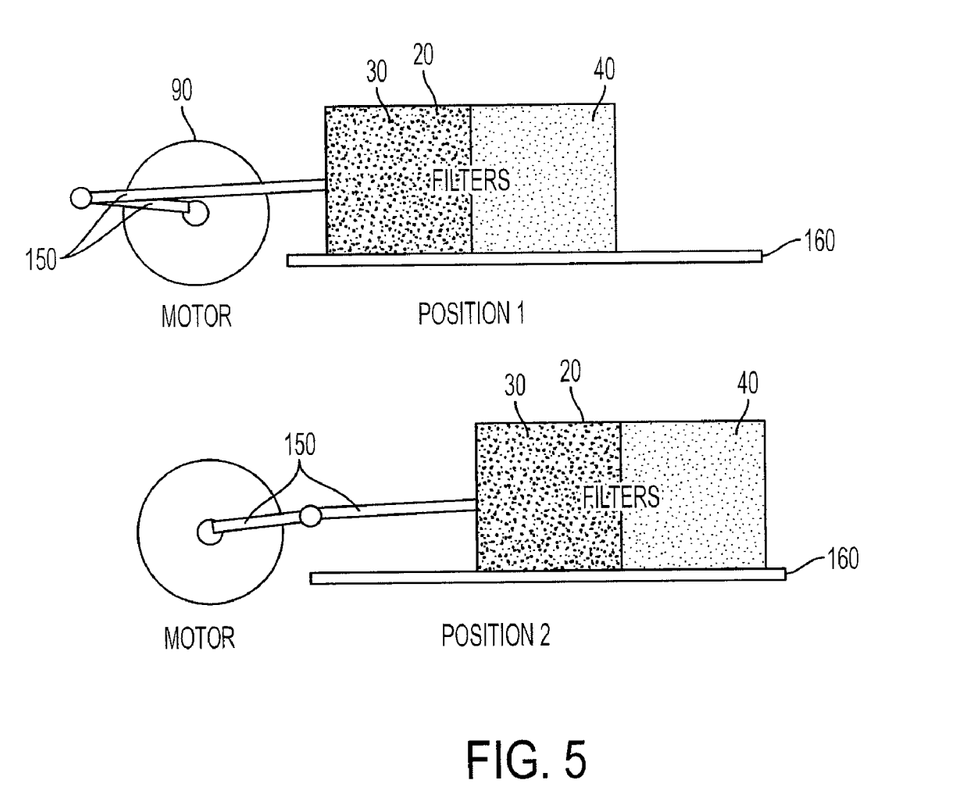
FIG. 5 shows an apparatus for changing the position of side-by-side filters, such that each is alternately moved in and out of position in front of a capturing lens, in accordance with an embodiment of the present invention.

In another embodiment, the filter segments are located on a side-by-side filter, designated as 20. The side-by-side filter 20 is shown in FIG. 5. As shown, an on-line filter segment 30 and an off-line filter segment 40 are located on respective sides of the side-by-side filter. The side-by-side filter 20 is disposed on a slotted platform, designated as 160. A mechanical device 90, such as a motor 90, alternately positions one filter segment in front of optics 100 (FIG. 4) and then the other filter segment in front of the optics using mechanical arm 150. The rest of the image capture and processing proceeds as shown in FIG. 4, with an imager, an image processing unit, and a display.

Figure 6A:
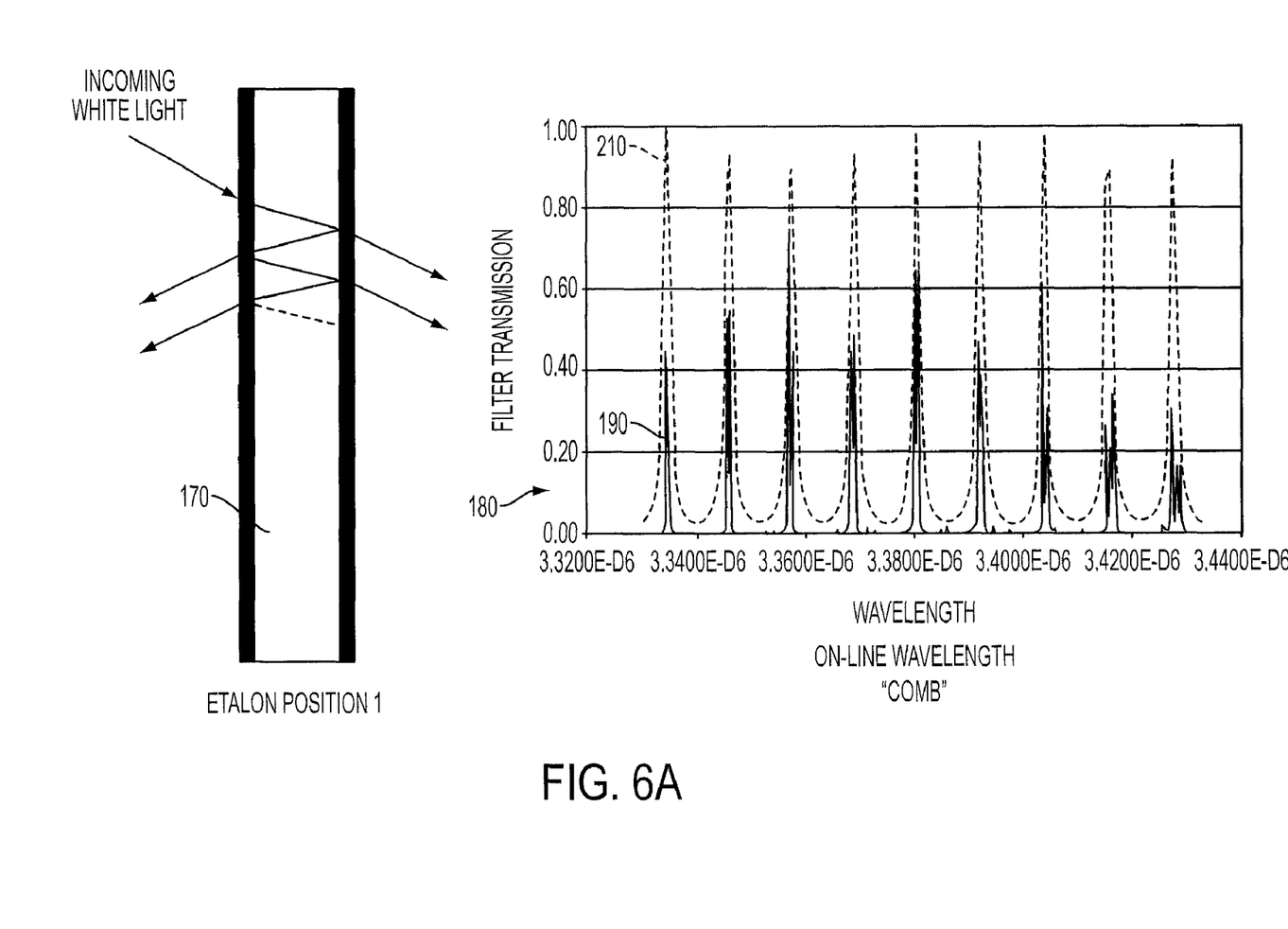
FIGS. 6A and 6B show an etalon used, in accordance with an embodiment of the present invention, to form an on-line response and an off-line response for an incoming light, by changing the angle of the etalon to provide interference patterns that are in phase and out of phase with respect to periodic absorption features of a target gas.
Figure 6B:
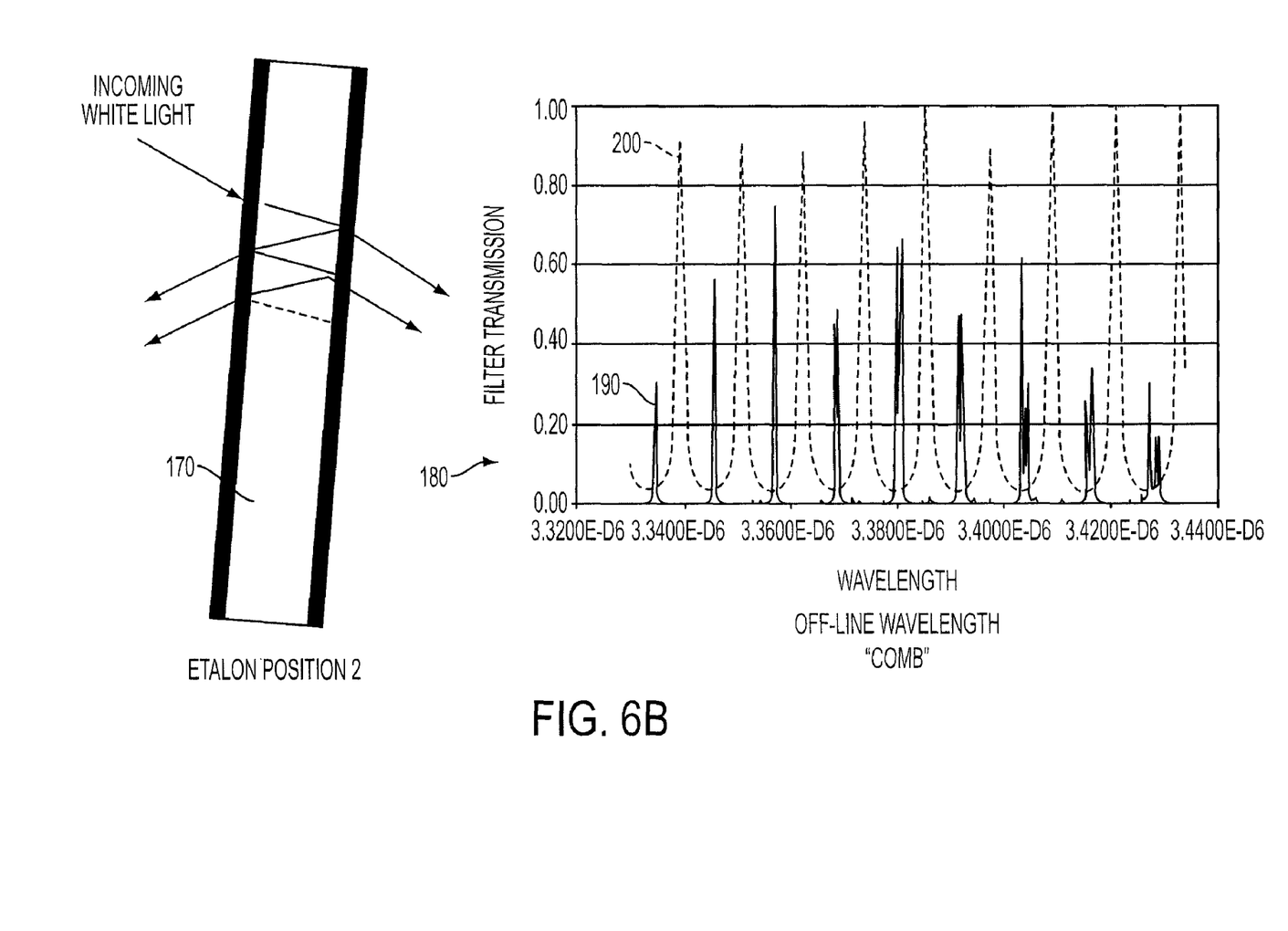

FIG. 6 shows another filter embodiment of the present invention including an etalon. The etalon, which is shown designated as 170, is used to form an on-line response and an off-line response for an incoming light. This is accomplished by changing the angle of etalon 170 with respect to a horizontal line. The angle is varied between position 1 (FIG. 6A) and position 2 (FIG. 6B), so that interference patterns are formed that are in phase and out of phase with respect to periodic absorption features of a target gas. The angle of the etalon may vary from approximately 0.5 degrees to 10 degrees between position 1 and position 2. The angle may be varied using a piezoelectric actuator, for example.

The interference patterns are illustrated in a spectral plot 180, which shows the periodic spectral response of a gas, such as ethane and methane. The spectral response of the gas is designated as 190. Also shown are two periodic etalon transmission functions. The first transmission function 190 represents a comb filter for the on-line wavelengths of the gas; the second transmission function 200 represents another comb filter (note the shift in wavelengths) for the off-line wavelengths of the gas. A comparison between the integrated on-line (in phase) and integrated off-line (out of phase) responses may be used to determine the presence or absence of the particular gas of interest.

The following table lists an exemplary parts list corresponding to the numerical designations in the figures:

| | PARTS LIST |
|---|---|
| 1 | Infrared radiation source |
| 2 | Infrared light beam |
| 3 | Gas |
| 4 | Lens |
| 5 | Single filter or filter wheel |
| 6 | Detector |
| 10 | Rotating filter wheel |
| 20 | Side-by-side filter |
| 30 | On-line filter element 1 |
| 40 | Off-line filter element 1 |
| 50 | On-line filter element 2 |
| 60 | Off-line filter element 2 |
| 70 | On-line filter element 3 |
| 80 | Off-line filter element 3 |
| 90 | Motor |
| 100 | Optics |
| 110 | Detector Array |
| 120 | Clocking Device |
| 130 | Image Processing Unit |
| 140 | Display |
| 150 | Mechanical Arm |
| 160 | Slotted Platform |
| 170 | Etalon |
| 180 | Spectral Plot |
| 190 | Periodic feature in gas spectrum |
| 200 | Periodic etalon off-line transmission function |
| 210 | Periodic etalon on-line transmission function |

Although the invention is illustrated and described herein with reference to specific embodiments, the invention is not intended to be limited to the details shown. Rather, various modifications may be made in the details within the scope and range of equivalents of the claims.

What is claimed is:
1. A system for imaging a target gas comprising:
a movable filter, positioned along a line-of-sight to the target gas, for receiving energy from the target gas,
the movable filter including at least two filter segments, one filter segment passing energy corresponding to an on-line wavelength of the target gas, and another filter passing energy corresponding to an off-line wavelength of the target gas, and
an imager for sequentially imaging the energy passed through the one filter segment, corresponding to the on-line wavelength of the target gas, and the other filter segment, corresponding to the off-line wavelength of the target gas;
wherein the movable filter includes at least two sets of filter segments,
a first set including an on-line filter segment and an off-line filter segment, and
a second set including another on-line filter segment and another off-line filter segment, and
the first set passes an on-line wavelength and an off-line wavelength of a first target gas during a first interval of time, and
the second set passes an on-line wavelength and an off-line wavelength of a second target gas during a second interval of time.

2. The system of claim 1 wherein
the movable filter includes a rotating wheel filter partitioned into the at least two sets of filter segments.

3. The system of claim 1 wherein
the imager is configured to image the energy passed through the movable filter passively, and without any active signal transmission to the target gas.

4. The system of claim 1 further including
an image processing unit for receiving images captured by the imager of the energy passed through the movable filter, and
the image processing unit configured to determine presence or absence of the target gas, based on computations of multiple concentration path lengths (CPLs) corresponding to multiple pixels of the imager.

5. The system of claim 4 further including
a clocking unit controlled by the image processing unit for synchronizing the images captured by the imager with movements of the movable filter.

6. The system of claim 1 wherein
the target gas includes a hydrocarbon having at least one on-line wavelength and at least one off-line wavelength.

7. A system for imaging a target gas comprising:
a movable filter, positioned along a line-of-sight to the target gas, for receiving energy from the target gas,
the movable filter including at least two filter segments, one filter segment passing energy corresponding to an on-line wavelength of the target gas, and another filter passing energy corresponding to an off-line wavelength of the target gas, and
an imager for sequentially imaging the energy passed through the one filter segment, corresponding to the on-line wavelength of the target gas, and the other filter segment, corresponding to the off-line wavelength of the target gas;
wherein the movable filter includes an etalon for filtering the received energy including white light,
the etalon is configured for tilting between a first angle and a second angle, and
the etalon is configured to provide an on-line comb filter when tilted to the first angle, and provide an off-line comb filter when tilted to the second angle.

8. The system of claim 7 wherein
the target gas is characterized by a periodic signal in the frequency domain,
the on-line comb filter includes a comb-like structure for filtering the target gas, when the etalon is tilted to the first angle, and
the off-line comb filter includes a similar comb-like structure for filtering the target gas, when the etalon is tilted to the second angle.

9. A system for detecting gas emission comprising:
a movable filter for receiving passive energy from the gas,
the movable filter including a first segment for passing energy from the fugitive gas characterized by an on-line wavelength corresponding to an absorption feature of the gas,
the movable filter including a second segment for passing energy from the gas characterized by an off-line wavelength corresponding to a non-absorption feature of the gas, and
an imager for imaging the energy sequentially passed from the first segment and the second segment;
wherein the movable filter includes an etalon for filtering the received energy,
the etalon is configured for moving between a first angle and a second angle, and
the etalon is configured to provide an on-line comb filter when moved to the first angle, and provide an off-line comb filter when moved to the second angle.

10. The system of claim 9 wherein
the movable filter includes a rotating filter wheel, or a side-by-side filter,
the rotating filter wheel and the side-by-side filter partitioned into segments including at least the first and second segments.

11. The system of claim 10 further including
an image processing unit for receiving images captured by the imager of the energy sequentially passed by the first and second segments, and
the image processing unit configured to determine presence or absence of the gas, based on computations of multiple concentration path lengths (CPLs) corresponding to multiple pixels of the imager.

12. The system of claim 11 further including
a clocking unit controlled by the image processing unit for synchronizing the images captured by the imager with the sequential passing of energy from the first and second segments.

13. The system of claim 9 wherein
the gas is characterized by a periodic signal in the frequency domain,
the on-line comb filter includes a comb-like structure for filtering the gas, when the etalon is moved to the first angle, and
the off-line comb filter includes a similar comb-like structure for filtering the gas, when the etalon is moved to the second angle.

14. A passive system for imaging a target gas comprising:
a movable filter, positioned along a line-of-sight to the target gas, for passively receiving energy from the target gas,
the movable filter including at least two filter segments, one filter segment passing energy corresponding to an on-line wavelength of the target gas, and another filter passing energy corresponding to an off-line wavelength of the target gas, and
an imager for sequentially and passively imaging the energy passed through the one filter segment, corresponding to the on-line wavelength of the target gas, and the other filter segment, corresponding to the off-line wavelength of the target gas, wherein the movable filter includes a side-by-side filter partitioned into an on-line filter segment and an off-line filter segment, and the on-line filter segment passes the on-line wavelength during a first interval of time, and the off-line filter segment passes the off-line wavelength during a second interval of time.

15. The system of claim 14 wherein
the on-line wavelength of the target gas corresponds to an absorption wavelength, and
the off-line wavelength of the target gas corresponds to a non-absorption wavelength.

16. The system of claim 14 wherein
the movable filter includes a rotating wheel filter partitioned into the at least two filter segments, and
the one filter segment passes the on-line wavelength during a first interval of time, and the other filter segment passes the off-line wavelength during a second interval of time.

17. The system of claim 14 wherein
the movable filter includes at least two sets of filter segments,
 a first set including an on-line filter segment and an off-line filter segment, and
 a second set including another on-line filter segment and another off-line filter segment, and
the first set passes an on-line wavelength and an off-line wavelength of a first target gas during a first interval of time, and
the second set passes an on-line wavelength and an off-line wavelength of a second target gas during a second interval of time.

18. The system of claim 14 wherein
the movable filter includes an etalon for filtering the received energy including white light,
the etalon is configured for tilting between a first angle and a second angle, and
the etalon is configured to provide an on-line comb filter when tilted to the first angle, and provide an off-line comb filter when tilted to the second angle.

19. The system of claim 14 further including
an image processing unit for receiving images captured by the imager of the energy passed through the movable filter, and
the image processing unit configured to determine presence or absence of the target gas, based on computations of multiple concentration path lengths (CPLs) corresponding to multiple pixels of the imager.

* * * * *